United States Patent [19]

Chalk et al.

[11] Patent Number: 4,467,118

[45] Date of Patent: Aug. 21, 1984

[54] PROCESS FOR THE CATALYTIC SYNTHESIS OF CONJUGATED DIENES FROM DIALKYLALLYLAMINES

[75] Inventors: Alan J. Chalk, Kinnelon; Steven A. Magennis, Wayne; Vasile S. Wertheimer; Richard E. Naipawer, Wallington, all of N.J.

[73] Assignee: Givaudan Corporation, Clifton, N.J.

[21] Appl. No.: 354,322

[22] Filed: Mar. 3, 1982

[51] Int. Cl.$^3$ .................. C07C 1/32; C07C 11/12; C07C 33/02; C07C 41/18; C07C 43/15; C07D 307/06; C07D 309/04

[52] U.S. Cl. .................. 568/687; 549/356; 549/429; 568/626; 568/813; 568/873; 568/875; 568/903; 585/469; 585/534; 585/603

[58] Field of Search ............... 568/687, 902, 903, 626, 568/813, 873, 875; 549/356, 509, 429; 585/534, 603, 469

[56] References Cited

U.S. PATENT DOCUMENTS

| | | | |
|---|---|---|---|
| 2,719,872 | 10/1955 | Happel et al. | 585/534 |
| 3,670,032 | 6/1972 | Romanelli | 568/903 |
| 3,922,299 | 11/1975 | Heck | 568/902 |
| 3,932,539 | 2/1972 | Kane et al. | 568/875 |
| 4,188,498 | 2/1980 | Murata et al. | 568/875 |
| 4,266,087 | 5/1981 | Chalk et al. | 568/875 |

FOREIGN PATENT DOCUMENTS 1107865  3/1968  United Kingdom ............... 549/356

*Primary Examiner*—Natalie Trousof
*Assistant Examiner*—Patricia M. Scott
*Attorney, Agent, or Firm*—Robert F. Tavares

[57] ABSTRACT

There is disclosed a novel process for converting allylic amines, having a hydrogen bonded to a carbon δ to the amino group, to a diene in the presence of a zero valent palladium phosphine complex and a weak acid. The process has been used to make novel compositions containing 7-methoxy-3,7-dimethyloctadienes which are useful as odorants and flavorants.

7 Claims, No Drawings

PROCESS FOR THE CATALYTIC SYNTHESIS OF CONJUGATED DIENES FROM DIALKYLALLYLAMINES

BACKGROUND OF THE INVENTION

1. Field of the Invention
Dienes from allylic amines.

2. The Prior Art
Allylic amines having a hydrogen bonded to a carbon δ to the amino group have been converted to dienes by a Hofmann Elimination reaction according to the general reaction

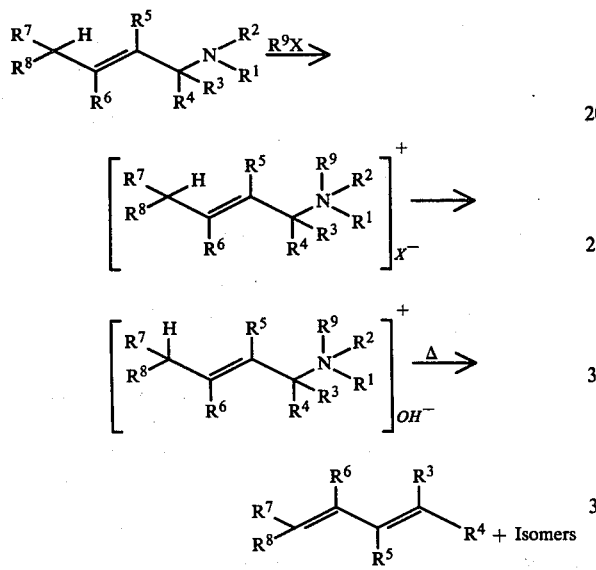

The R groups are suitable reaction inert substituents.

As illustrated, the normal Hofmann elimination is a multistep process which involves converting a trialkyl amine to a quaternary salt (such as a tetraalkyl ammonium halide or sulfate), converting said salt to a trialkyl ammonium hydroxide which is decomposed to form the diene.

SUMMARY OF THE INVENTION

This invention discloses a process, both novel and unexpected, which allows for the conversion of an allylic amine to a diene without first preparing a quaternary salt. In a one step process, the allylic amine is converted to a diene by reacting said amine in the presence of a zero valent palladium phosphine complex and a weak acid having a pKa greater than 2. The method can be applied generally to allylic amines having at least one allylic hydrogen δ to the amine nitrogen. The process can be illustrated as follows:

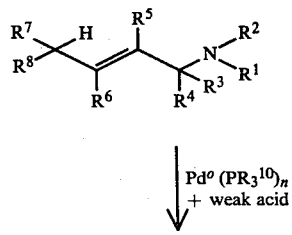

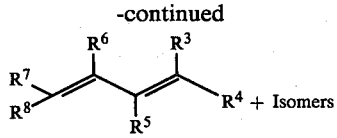

wherein the R groups are suitable reaction inert substituents, suitable members of which are defined below. The nature of the isomers obtained would depend on either the nature of $R^5$ and $R^6$ or the propensity of the dienes to isomerize in the presence of the catalyst. For example, if $R^5$ or $R^6$ is bonded to the double bond by an $sp^3$ carbon which also has a hydrogen, that hydrogen may be lost rather than the one indicated above. Similarly, if the diene first formed has an allylic hydrogen, it may be subject to further isomerization to form a new diene.

Both of these phenomena can be illustrated by observing what occurs when N,N-dialkylgeranylamine is subjected to the process of this invention as shown below:

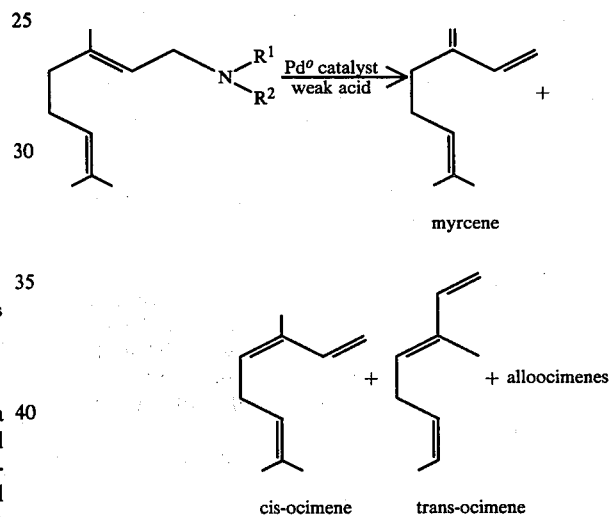

It appears that the N,N-dialkylgeranylamine is first converted to a mixture of myrcene and the cis and trans ocimenes which are the primary products, each depending upon the particular allylic hydrogen that is abstracted. If the reaction is allowed to continue, it appears that the myrcene isomerizes to cis and trans ocimenes which in turn may isomerize to a mixture of alloocimenes. Thus, the number of isomers obtained in the final product is a function of the nature of the starting material and the reaction time.

This invention also provides a number of novel mixtures which are useful fragrance materials, particularly those derived from 7-hydroxygeranylamine, 7-hydroxynerylamine, 7-methoxygeranylamine and 7-methoxynerylamine, which are characterized by substantial amounts of the normally difficult to obtain alloocimene derivatives. Preferred are the 7-methoxyocimenes, 7-methoxyalloocimenes and novel mixtures thereof. Especially preferred are E,E-7-methoxyalloocimene and mixtures containing same which are particularly valuable in fragrance compositions for imparting celery-like, green, lime notes.

DESCRIPTION OF THE PREFERRED EMBODIMENTS

The process of this invention is very general. In its broader aspects, the process can be illustrated as follows:

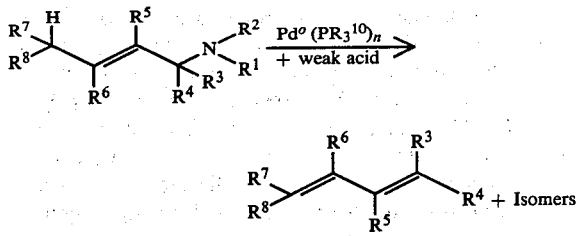

wherein:

$R^1$ and $R^2$ may be alike or different and can be chosen from the group consisting of lower alkyl (e.g. $C_1$ to $C_4$) or together form a cyclic moiety (e.g. morpholinyl or piperidinyl)

$R^3$ through $R^8$ are the same or different and can be chosen from the group consisting of hydrogen, alkyl radicals, alkenyl radicals, alkynyl radicals, aromatic radicals and the like (e.g. H, $CH_3-$, $C_2H_5-$, $C_3H_7-$, $C_4H_9-$, $H_2C=CH-$, $(CH_3)_2C=CH-$, $C_6H_5CH_2-$, etc.) or substituted derivatives thereof (e.g. $HO-C(CH_3)_2CH_2-$, $CH_3O-C(CH_3)_2-CH_2-$, etc.)

$R^{10}$ may be phenyl, substituted phenyl, alkyl (e.g. lower alkyl, $C_1$ to $C_4$) cycloalkyl (e.g. cyclohexyl)

The process has broad application and can essentially be applied to just about any allylic amine wherein the amino group is fully substituted (tertiary) and there is at least one allylic hydrogen on a carbon δ to said nitrogen. It is more practical and preferred, however, to apply it to more common and readily available allylic amines such as N,N-dialkylgeranylamines, N,N-dialkylnerylamines, and the 7-hydroxy and 7-alkoxy-derivatives thereof.

In the preferred practice of this invention, a compound of the formula

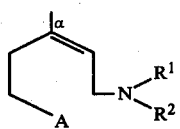

wherein:

represents dimethylamino, diethylamino, dipropyl amino, di-n-butylamino, piperidinyl, morpholinyl or pyrrolidinyl; the double bond α can be E or Z; and the group A represents $(CH_3)_2C=CH-$, $HO-C(CH_3)_2C-H_2-$ or $CH_3O-C(CH_3)_2-CH_2-$; is heated in the presence of a zero valent palladium phosphine complex and a weak acid having a pKa greater than 2.

While not wishing to be bound by any theory, it is well accepted in the art that zero valent palladium phosphine complexes are produced when palladium salts are reduced in the presence of phosphines. Any palladium salt, mixed with a tertiary phosphine, may be reduced in situ using reducing agents known in the art (e.g. hydrazine, silicon hydrides, etc.). It should be mentioned that commercially available zero valent palladium phosphine complexes such as tetrakis triphenyl phosphine palladium zero are suitable but less preferred as too expensive.

Especially preferred, however, is to use a readily available palladium salt which can be reduced to palladium zero in the presence of a phosphine without adding any additional reducing agents. For example, the palladium carboxylates are so reduced without the need for any additional reducing agents and, among these, the more economical and readily available palladium acetate is especially preferred. Under the conditions of this reaction, palladium chloride can also be converted to palladium zero in the presence of a phosphine without the need of additional reducing agents and is also especially preferred.

The phosphine used is a tertiary phosphine, $PR_3$, wherein R may represent phenyl, substituted phenyl, alkyl (preferably from four to twelve carbons), cycloalkyl (e.g. cyclohexyl). In the preferred process, the palladium salt is reduced in the presence of an excess of phosphine. It is preferred to use about three to twenty moles of phosphine per mole of palladium salt, with four to ten moles of phosphine per mole of palladium being especially preferred.

If the palladium salt is one that requires a reducing agent other than the phosphine, the zero valent palladium complex is normally prepared before adding the allylic amine. In the especially preferred process, however, a palladium salt is used which does not require adding additional reducing agents, and it is preferred to simply mix the palladium salt and the phosphine together with the starting allylic amine and weak acid and heat the mixture.

The required acid is preferably a weak acid having a pKa in the range 2–10 with acids having a pKa in the range 3–6 being especially preferred. Among these are organic carboxylic acids (e.g. acetic acid, propionic acid, benzoic acid, chloroacetic acid, etc.) and the salts of strong acids (e.g. HCl) with weak bases (e.g. $NH_3$, amines, etc.), typical salts being for example ammonium chloride, triethyl ammonium chloride, etc.

The palladium is used in catalytic amounts. It is preferred to use about 1 mole of palladium for every 300 to 5,000 moles of allylamine to be converted, without about 1 mole of palladium per 500 to 2,000 moles of allylamine being especially preferred.

It is preferred to use one to ten moles of acid per mole of allylamine to be converted, with two to five moles of acid per mole of allylamine being especially preferred.

The process requires nothing more than reacting the mixture (i.e. the zero valent palladium phosphine complex, the allylic amine and the weak acid) at the desired temperature for the desired time.

As indicated, the reaction is carried out at elevated temperatures with a temperature range of 100° C. to 150° C. being preferred with 110° C. to 140° C. being especially preferred.

The reaction can be followed by vapor phase chromatography or any other suitable analytical method. By this method one can stop the reaction when the desired reaction mix is obtained or allow it to continue until isomerized further.

Alternatively, one can reduce the amount of isomerization by removing the primary products as formed, for example by steam distillation.

The 7-alkoxyocimenes, the 7-alkoxyalloocimenes, and the mixtures thereof which can be prepared by the instant process are novel and are useful ingredients for the preparation of fragrance bases for perfumes, colognes, and the like. Preferred are the 7-methoxy compounds and mixtures thereof with the E,E-7-methoxyalloocimene being especially preferred.

The E,E-3,7-dimethyl-7-methoxyocta-2,4-diene (E,E-7-methoxyalloocimene) is the especially preferred isomer and has a fresh lime, green, celery odor which makes it especially useful in fragrance compositions and in fruit, vegetable, and spice flavors. While this compound is especially preferred, it is more practical to use a mixture of isomers as is produced by the process of this invention. The cis and trans-methoxyocimenes have celery and lime notes which are compatible with the alloocimene and a mixture of the ocimenes and alloocimene when used in place of the alloocimene provides a similar effect. Small amounts of methoxymyrcene, which has a linalool, lime type of odor, can also be present.

Depending on the needs and preferences of the perfumer and the ability of the process to provide mixtures having such components at various concentrations, a number of mixtures can be provided. Those mixtures considered to be the most practical and preferred are those wherein the 7-methoxyalloocimene is present at a level of greater than 5% (preferably 20-35%); the 7-methoxyocimenes (cis and trans) is less than 85% (preferably 50-75%), and the methoxymyrcene is kept below about 10% (preferably 3-6%).

It is preferred to use such mixtures in a practical range of from about 0.1% to 20% of the fragrance base, but larger amounts can be used to produce special effects. For example, when a mixture consisting essentially of 4-5% 7-methoxymyrcene, 60-70% 7-methoxyocimenes, and 25-35% 7-methoxyalloocimene was used in a lavender fragrance for soap at a level of 12%, the composition was fresher and more rounded. It was found to blend well with the citrus and lavender notes while adding to the intensity of the composition and enhancing its fresh character. Similarly, when added to a floral fragrance base for lotions at about a 2% level, the addition of a fresh green note was noted. It was also found that the celery leaf character was such that concentrations of 90% were used in preparing celery base.

ILLUSTRATION OF THE PREFERRED EMBODIMENTS

The following examples are provided to illustrate the preferred embodiments as they are disclosed herein and are not to be construed as limiting.

Infrared spectra (ir) were recorded as neat samples on a Perkin-Elmer Model 457 spectrophotometer and absorptions are reported in inverse centimeters ($cm^{-1}$).

Molecular weights were determined on a Finnigan Model 4000 mass spectrometer.

Nuclear magnetic resonance (nmr) spectra were recorded as solutions in chloroform-$d_1$, using a Varian EM-360 proton spectrometer ($^1H$-nmr) and a Varian Model CFT-20 heteronuclear spectrometer ($^{13}C$-nmr), and are reported as δ units relative to tetramethylsilane (TMS) (0.0δ).

Gas-liquid chromatography (glc) was carried out on a 10% Carbowax®-20M (6 ft.×¼ in.) column using a Varian Model 2700 gas chromatograph with thermal conductivity detector (TC).

EXAMPLE 1

This example provides a general procedure for illustrating the process of this invention and to further illustrate how the product mixture changes due to isomerization with time. This is illustrated in the table below.

In this example 20.7 g of N,N-diethylnerylamine, 10 ml of acetic acid, 0.0224 g of palladium acetate and 0.210 g of triphenyl phosphine were held under nitrogen at 120° C.

TABLE I

| Time (hours) | Myrcene | Analysis of Converted Product | | | |
|---|---|---|---|---|---|
| | | Ocimenes | | Alloocimenes | |
| | | cis | trans | cis | trans |
| 0.5 | 45.8 | 26.2 | 25.2 | 0.8 | 2.0 |
| 1.0 | 33.2 | 29.3 | 31.3 | 1.7 | 4.6 |
| 2.0 | 20.6 | 30.8 | 35.7 | 3.0 | 9.8 |
| 3.0 | 7.6 | 24.7 | 31.3 | 7.8 | 28.7 |
| 5.5 | 5 | 12 | 18 | 15 | 50 |

The conversion of amine to products were approximately 50% after 2 hours and approximately complete after 5½ hours at 120° and 16 hours at 100° C. The product was steam distilled to give a 64% yield of dienes having the final composition shown above.

EXAMPLES 2 through 11

The following Table II illustrates the effect that changes in the amine have on the final product distribution.

TABLE II

Examples 2-11[a]

| Example | Starting amine[b] | Conversion % | Yield % | Product Composition % | | | | |
|---|---|---|---|---|---|---|---|---|
| | | | | Myrcene | Ocimenes | | Alloocimenes | |
| | | | | | cis | trans | cis | trans |
| 2 | 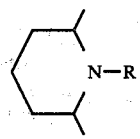 | 98 | 57.7 | 7.7 | 23.5 | 31.4 | 14.4 | 23.0 |
| 3 | iPr₂NR | 92.8 | 48.5 | 28.6 | 24.7 | 30.7 | 8.8 | 7.1 |
| 4 | nBu₂NR | 81.2 | 51.2 | 21.0 | 24.7 | 25.4 | 12.5 | 16.3 |

TABLE II-continued

Examples 2-11[a]

| Example | Starting amine[b] | Conversion % | Yield % | Product Composition % | | | | |
|---|---|---|---|---|---|---|---|---|
| | | | | Myrcene | Ocimenes cis | Ocimenes trans | Alloocimenes cis | Alloocimenes trans |
| 5 | ⟨cyclohexyl⟩N—R | 73.6 | 56.0 | 16.2 | 24.1 | 30.2 | 12.9 | 16.4 |
| 6 | Et₂NR | 71.4 | 53.2 | 11.3 | 22.2 | 28.8 | 13.3 | 24.5 |
| 7 | Me₂NR | 42.2 | 67.9 | 9.7 | 13.6 | 16.4 | 20.6 | 39.7 |
| 8 | ⟨cyclohexyl⟩N—R | 37.8 | 33.2 | 18.7 | 11.7 | 13.8 | 15.2 | 40.4 |
| 9 | Me₂NR' | 62.9 | 48.4 | 6.7 | 15.4 | 18.4 | 16.2 | 43.2 |
| 10 | ⟨cyclohexyl⟩N—R' | 58.0 | 50.8 | 4.0 | 10.1 | 17.6 | 12.2 | 56.1 |
| 11 | Et₂NR' | 56.6 | 39.3 | 14.6 | 21.3 | 29.9 | 10.7 | 23.5 |

[a]0.05 M amine; 0.15 M AcOH; 5.4 × 10⁻⁵ M Pd(OAc)₂; 5 × 10⁻⁴ M Ph₃P; 17 hrs. at 118° C.
[b]R = Geranyl, R' = Neryl

EXAMPLE 12

Example 1 was repeated except that 25 ml water was added and a distillation trap used which recycled the aqueous part of the distillate thus effecting a steam distillation. The volatile dienes were thus removed as formed. An 88% yield of dienes was obtained having the composition 61% myrcene, 17.5% cis and 21.1% trans-ocimene after 12½ hours at 120°. This illustrates that the primary products can be removed as formed and before they are isomerized.

EXAMPLE 13

Example 12 was repeated except that only 0.105 g triphenylphosphine was used and 22.6 g of N,N-diethyl-7-hydroxygeranylamine was used as the amine. After 9 hours at 120° there was obtained a yield of 11.7% 2,6,6-trimethyl-2-vinyltetrahydropyran, 29.6% myrcenol, 22.2% cis and 17.3% trans-ocimenol.

EXAMPLE 14

Example 13 was repeated except that 0.210 g triphenylphosphine was used and 22.6 g N,N-diethyl-7-hydroxynerylamine. After 17½ hours at 120° C. there was obtained a yield of 13.1% 2,6,6-trimethyl-2-vinyltetrahydropyran, 28.6% myrcenol, 16.1% cis-ocimenol, 21.9% trans-ocimenol.

EXAMPLE 15

Example 1 was repeated except that 22.6 g N,N-diethyl-7-hydroxygeranylamine was used as amine. The following results were obtained.

| Time Hours | Vinyl-pyran[a] | Tetra-hydro-furan[b] | 7-Hydroxy-myrcene | 7-Hydroxy-ocimenes cis | 7-Hydroxy-ocimenes trans | Starting Amine |
|---|---|---|---|---|---|---|
| 1 | 6 | 0 | 10 | 12 | 10 | 62 |
| 2 | 7 | 2 | 9 | 17 | 15 | 49 |
| 4 | 6 | 7 | 6 | 24 | 22 | 34 |
| 6 | 4 | 13 | 4 | 27 | 27 | 25 |
| 8 | 3 | 20 | 3 | 26 | 30 | 17 |

[a]2,6,6-Trimethyl-2-vinyltetrahydropyran
[b]2,2-Dimethyl-5-(but-2-en-2-yl)tetrahydrofuran After 9 hours at 120°, the product was distilled to give a yield of 5% 2,6,6-trimethyl-2-vinyltetrahydropyran, 31%, 2,2-dimethyl-5-(but-2-en-2-yl)tetrahydrofuran, 2.5% 7-hydroxymyrcene, 18% cis-7-hydroxyocimene, and 24.6% trans-7-hydroxyocimene.

EXAMPLE 16

Example 13 was repeated except that the acetic acid was replaced by 12 g benzoic acid. The reaction was similar but somewhat slower and the product contained a higher fraction of 2,6,6-trimethyl-2-vinyltetrahydropyran. Similar results were obtained with ammonium chloride or chloroacetic acid in place of benzoic acid, but ammonium sulfate and potassium bisulfate were ineffective.

EXAMPLE 17

N,N-Diethyl-7-Methoxygeranylamine

Into a flask was charged N,N-diethylgeranylamine (837.5 g) and methanol (1580 g).

Agitation was started and sulfuric acid (1020 g) was added slowly while keeping the temperature below 30° C. with cooling. After the addition of the acid, the ice bath was removed and the mixture was agitated slowly for 24 hours at room temperature. The mixture was then added in portions to a 22.5% NaOH solution (3700 g) under strong agitation. After the addition was completed and the aqueous layer checked for pH in excess of 9, the two layers were phase separated. In order to avoid foaming at the beginning of the distillation, the organic layer was dried over MgSO$_4$, filtered through filter aid, and the volatiles removed on a rotary evaporator. The crude product weighed 880–930 g. Fractionation of the crude product yielded 605 g of the desired product: bp 110° C. @ 2 mm Hg.

7-Methoxy-3,7-dimethyloctadienes

A mixture of 143.7 g N,N-diethyl-7-methoxygeranylamine, 102 g acetic acid, 1.7 g triphenylphosphine, 0.13 g palladium acetate, 0.7 g Irganox 1010 ®*(or other equivalent antioxidant) and 14.4 g dimethylacetamide was heated under nitrogen at 120° C. for 18 hours. Products were then distilled (222 g) at 5 mm Hg. The pot residue was reused by adding a further 143.7 g of the amine, 102 g acetic acid, 14.4 g dimethylacetamide, and the heating cycle repeated. The products obtained in 3 such cycles each of 18 hours were as follows:

| | | Product Composition % | | | |
|---|---|---|---|---|---|
| Cycle | % Yield | 7-Methoxy-myrcene | cis-7-Methoxy-ocimene | trans-7-Methoxy-ocimene | 7-Methoxy-alloocimene |
| 1 | 59 | 4.3 | 28.9 | 38.0 | 28.8 |
| 2 | 59 | 4.2 | 28.9 | 38.4 | 28.4 |
| 3 | 65.7 | 4.4 | 29.1 | 32.7 | 33.8 |

This example also illustrates that the catalyst can be reused.
*Registered Trademark of Ciba-Geigy Corp. {tetrakis[methylene-3-(3',5'-di-t-butyl-4'-hydroxyphenyl)propionate]methane}.

The product composition was further rectified by spinning band distillation on a Nester-Faust NFA 100 Auto-Annular Still. The methoxydienes were obtained in the purities indicated and where characterized by their spectral data.

7-Methoxymyrcene, (7-Methoxy-3-methylene-7-methyloct-1-ene)—98.9% bp 64°–64.5° C. (4.0 mm); mol wt 168 (ms); ir,1600 (s), 1382, 1365, 1083 (s) and 894 cm$^{-1}$; $^1$H-nmr 1.1δ(6H, s), 1.5 (4H, broad multiplet), 2.2δ (2H, broad complex), 3.1 (3H, s, methoxy), 5.0 (4H, complex) and 6.4 (1H, 2 d's, J=11 and 18 Hz).
Odor: linalool, lime.

cis-7-Methoxyocimene,[(Z) 3,7-Dimethyl-7-methoxyocta-1,3-diene]—83% bp 65.5°–66.5° C. (3.9 mm); mol wt 168 (ms); ir, 1382 (s), 1365 (s), 1060, 986 and 900 cm$^{-1}$; $^1$H-nmr 1.2δ (6H, s), 1.8 (3H, multiplet, olefinic methyl), 1.3–2.3 (6H, broad complex), 3.2 (3H, s, methoxy), 5.2 (3H, broad complex) and 6.9 (1H, broad multiplet); $^{13}$C-nmr 19.77δ (1C, q), 21.97 (1C, t), 25.02 (2C, q), 39.76 (1C, t), 49.12 (1C, q), 74.82 (1C, s), 113.16 (1C, t), 131.16 (1C, d), 133.66 (1C, d) and 141.64 (1C, s).
Odor: lime, celery, slightly linalool.

trans-7-Methoxyocimene ](E) 3,7-Dimethyl-7-methoxyocta-1,3-diene]—85% bp 64.5° C. (3.7 mm); mol wt 168 (ms); ir, 1640, 1608, 1382, 1365, 1082, 988 and 890 cm$^{-1}$; $^1$H-nmr, 1.2δ (6H, s), 1.7 (3H, multiplet, olefinic methyl), 1.3–2.4 (4H, broad complex), 3.2 (3H, s, methoxy), 5.2 (3H, broad complex) and 6.4 (1H, 2d's, J=9 and 18 Hz); $^{13}$C-nmr, 11.58δ (1C, q), 22.84 (1C, t), 25.01 (2C, q), 39.41 (1C, t), 49.11 (1C, q), 74.32 (1C, s), 110.39 (1C, t), 133.16 (1C, d), 133.94 (1C, s) and 141.64 (1C, d).
Odor: celery, lime.

7-Methoxyalloocimene [(E,E) 3,7-Dimethyl-7-methoxyocta-2,4-diene]—80% bp 67° C. (3.5 mm); mol wt 168 (ms); ir, 1678 (s), 1630, 1382 (s), 1365 (s), 1080 and 968 cm$^{-1}$; $^1$H-nmr, 1.2δ (6H, s), 1.7 (6H, broad s, olefinic methyls), 2.2 (2H, 2d's, J=3 and 6 Hz, allylic methylene), 3.2 (3H, s, methoxy), 5.5 (2H, broad multiplet) and 6.1 (1H, d, J~15 Hz, olefinic H at C-4); $^{13}$C-nmr, 12.14δ (1C, q), 13.66 (1C, q), 24.84 (2C, q), 43.51 (1C, t), 49.19 (1C, q), 75.01 (1C, s), 122.50 (1C, d), 122.50 (1C, d), 124.91 (1C, d), 134.45 (1C, s) and 137.44 (1C, d).
Odor: fresh lime, green, celery.

EXAMPLE 18

Tributylphosphine was substituted for triphenylphosphine in an experiment similar to Example 6. The reaction mixture contained 0.10 g tributylphosphine, 0.012 g Pd(OAc)$_2$, 10.6 g N,N-diethylgeranylamine, 8.7 ml acetic acid and 1.0 g of tridecane as internal standard. After 24 hours at 118° C. a conversion of 37% was obtained with a yield of 20%. The product composition was 56% myrcene, 16% cis-ocimene, 20% trans-ocimene, 6% cis-alloocimene, and 2% trans-alloocimene.

EXAMPLE 19

48.2 g (0.2 mole) N,N-Diethyl-3,7-dimethyl-7-methoxy-2-octenylamine, 13.2 g (0.22 mole) acetic acid, 0.045 g palladium acetate and 0.42 g triphenylphosphine were stirred under nitrogen at 120° C. for ½ hour after which 35 ml water was added and the mixture was steam distilled. There was obtained a mixture of 54.8% methoxymyrcene, 16.2% cis-methoxyocimene. and 29.0% trans-methoxyocimene. The overall yield was 74.8%.

This example illustrates how isomerization can be minimized by removing the product after a short reaction time. (Compare with Example 17). Similar results were obtained whether the Z or E isomer was used as the starting material.

EXAMPLE 20

| Lavender Soap Fragrance | |
|---|---|
| | Parts per thousand |
| Coumarin | 40 |
| Benzaldehyde | 2 |
| Benzyl Acetate Extra | 80 |
| Geranium Algerian | 30 |
| Lavender 40/42 | 120 |
| Lavender Spike Spanish | 120 |
| Lavandin Pure | 320 |
| Oakmoss SR | 18 |
| Patchouli Oil | 15 |
| Rosemary Oil | 60 |
| Ambersage ® *(4,7-dihydro-2-isopentyl-2-methyl-1,3-dioxepin) | 75 |
| | 880 |

*Registered Trademark of Givaudan Corporation

The addition of 120 parts of the product composition, as described in Example 17, to the lavender soap fragrance enhanced the fresh character of the fragrance, adding to its overall intensity while blending well with the citrus and lavender notes.

EXAMPLE 21

| Floral Lotion Fragrance | Parts per thousand |
|---|---|
| Fixolide ® *(7-acetyl-1,1,3,4,4,6-hexamethyl-tetralin) | 30 |
| Heliotropin (Piperonal) | 60 |
| Indolarome ® **[4,5(1',2'-indano)-1,3-dioxane] (10% in dipropylene glycol) | 40 |
| Amyl Cinnamic Aldehyde | 15 |
| Aubepine | 30 |
| Benzyl Acetate Extra | 110 |
| Styrax Polko Oil | 20 |
| Eugenol Extra | 10 |
| Lilial ® *(p-t-butyl-2-methyldihydrocinnamaldehyde) | 220 |
| Linalool synthetic | 30 |
| Phenylethyl Alcohol | 100 |
| Terpineol Extra | 200 |
| Linalyl Acetate | 40 |
| Tuberose Multiflor | 13 |
| Ylang #3 | 40 |
| Leaf Alcohol | 2 |
| Dipropylene Glycol | 20 |
| | 980 |

*Registered Trademark of Givaudan Corporation
**Registered Trademark of International Flavors and Fragrances The addition of 20 parts of the product composition, as described in Example 17, to the floral lotion fragrance, added a fresh green note.

We claim:

1. A method for converting an allylic amine to a diene, said amine having at least one allylic hydrogen on a carbon "delta" to the amino nitrogen, which comprises heating said amine in the presence of a zero valent palladium phosphine complex and a weak acid having a pKa in the range 2–6, at a temperature between 100° C. and 150° C.

2. A process according to claim 1, wherein the allylic amine is of the formula

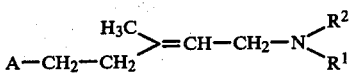

wherein:

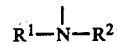

represents a dimethylamino, diethylamino, dipropylamino, di-n-butylamino, piperidenyl, morpholinyl, or pyrrolidinyl radical;
the olefinic bond may be E or Z; and,
A represents 2-methylpropenyl, 2-hydroxy-2-methylpropyl, or 2-methoxy-2-methylpropyl.

3. A process according to claim 1 or 2 wherein the allylic amine is heated with
(a) palladium acetate or palladium chloride
(b) a trisubstituted phosphine
(c) an acid having a pKa in the range 3–5 at a temperature between 110° C. and 150° C.

4. A process according to claim 1 or 2 wherein the allylic amine is heated with
(a) palladium acetate or palladium chloride
(b) a trisubstituted phosphine chosen from the group consisting of triphenyl phosphine and trialkylphosphines wherein the alkyl group has from four to twelve carbons
(c) an acid having a pKa in the range 3–5 at a temperature between 110° C. and 140° C.

5. A process according to claim 4 wherein for each mole of allylic amine there is used
(a) between $2 \times 10^{-4}$ to $3.3 \times 10^{-3}$ moles of palladium acetate or palladium chloride
(b) $6 \times 10^{-4}$ to $6.6 \times 10^{-2}$ moles of phosphine,
(c) 1 to 10 moles of acid.

6. A process according to claim 4 wherein for each mole of allylic amine there is used
(a) $5 \times 10^{-4}$ to $2 \times 10^{-3}$ molar equivalents of palladium acetate or palladium chloride,
(b) $2 \times 10^{-3}$ to $2 \times 10^{-2}$ molar equivalents of triphenyl phosphine,
(c) 2 to 5 molar equivalents of acetic acid.

7. A process according to claim 6 wherein A is 2-methoxy-2-methylpropyl.

* * * * *